United States Patent
von der Fecht et al.

(10) Patent No.: US 6,503,518 B1
(45) Date of Patent: Jan. 7, 2003

(54) REDUCED LIPID FLOWABLE PREPARATIONS

(75) Inventors: Stephanie von der Fecht, Schenefeld (DE); Gunhild Hamer, Hamburg (DE); Günther Schneider, Hamburg (DE); Andreas Bleckmann, Ahrensburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/581,413

(22) PCT Filed: Jan. 7, 1999

(86) PCT No.: PCT/EP99/00041

§ 371 (c)(1),
(2), (4) Date: Jun. 12, 2000

(87) PCT Pub. No.: WO99/37282

PCT Pub. Date: Jul. 29, 1999

(30) Foreign Application Priority Data

Jan. 22, 1998 (DE) .......................................... 198 02 206

(51) Int. Cl.$^7$ ............................ A61K 7/00; A61K 7/06; A61K 7/32
(52) U.S. Cl. ........................... 424/401; 424/60; 424/65; 424/70.9; 424/70.19; 514/938
(58) Field of Search ....................... 424/401, 59, 70.19; 514/844, 938

(56) References Cited

U.S. PATENT DOCUMENTS 5,770,185 A * 6/1998 Wachter et al. ............... 424/65

FOREIGN PATENT DOCUMENTS

| DE | 25 11 600 A | 9/1976 |
| DE | 27 34 059 A | 2/1979 |
| DE | 38 20 693 A | 12/1989 |
| FR | 1 437 366 | 7/1966 |

OTHER PUBLICATIONS

G. Prosperio et al.: "Neuere "essbare" O/W–Emulgator–Mischungen" Riechstoffe Aromen Kosmetica (RAK)., Bd. 28, Nr. 1, 1978, Seiten 8–12, XP002112591 Fachverlag V. Frankenstein. Eschershausen., DE Seite 10, recite spate—Seite 11, linke Spalte.

* cited by examiner

Primary Examiner—Russell Travers
Assistant Examiner—Alysia Berman
(74) Attorney, Agent, or Firm—Norris McLaughlin & Marcus

(57) ABSTRACT

Low-viscosity cosmetic or dermatological preparations comprising (I) one or more partially neutralized esters of monoglycerides and/or diglycerides of saturated fatty acids with citric acid, (II) one or more fatty alcohols chosen from the group of branched and unbranched alkyl alcohols having 12 to 40 carbon atoms, (III) a water phase, (IV) from 0 to 10% by weight of a lipid phase, based on the total weight of the preparations, where the weight ratio of the sum of the constituents from (I) and (I): (IV) is chosen from the range from 20:1 to 1:5.

11 Claims, No Drawings

REDUCED LIPID FLOWABLE PREPARATIONS

The present invention relates to cosmetic and dermatological preparations, in particular those of the oil-in-water type, to processes for their preparation and to their use for cosmetic and medicinal purposes.

The human skin is man's largest organ and performs a number of vital functions. Having an average area of about 2 $m^2$ in adults, it has a prominent role as a protective and sensory organ. The purpose of this organ is to transmit and avert mechanical, thermal, actinic, chemical and biological stimuli. In addition, it has an important role as a regulatory and target organ in human metabolism.

The main aim of skin care in the cosmetics sense is to strengthen or rebuild the skin's natural function as a barrier against environmental influences (e.g. dirt, chemicals, microorganisms) and against the loss of endogenous substances (e.g. water, natural fats, electrolytes), and also to assist its horny layer in its natural regeneration ability where damage has occurred.

If the barrier properties of the skin are impaired, increased resorption of toxic or allergenic substances or infection by microorganisms may result, leading to toxic or allergic skin reactions.

Another aim of skin care is to compensate for the loss by the skin of sebum and water caused by daily washing. This is particularly important if the natural regeneration ability is inadequate. Furthermore, skin care products should protect against environmental influences, in particular against sun and wind, and delay skin ageing.

Medicinal topical compositions usually comprise one or more medicaments in an effective concentration. For the sake of simplicity, in order to clearly distinguish between cosmetic and medicinal use and corresponding products, reference is made to the legal provisions in the Federal Republic of Germany (e.g. Cosmetics Directive, Foods and Drugs Act).

The term emulsion generally means heterogeneous systems which consist of two liquids which are immiscible or miscible with one another only to a limited extent, which are usually referred to as phases. In an emulsion, one of the two liquids is dispersed in the form of very fine droplets in the other liquid.

If the two liquids are water and oil and oil droplets are very finely dispersed in water, this is an oil-in-water emulsion (O/W emulsion, e.g. milk). The basic character of an O/W emulsion is determined by the water. In the case of a water-in-oil emulsion (W/O emulsion, e.g. butter), the principle is reversed, the basic structure being determined here by the oil.

The person skilled in the art is of course aware of a large number of ways to formulate stable O/W preparations for cosmetic or dermatological use, for example in the form of creams and ointments which can be spread in the range from room temperature to skin temperature, or as lotions and milks, which are more likely flowable in this temperature range. However, the prior art recognizes only a few formulations which are of such low viscosity that they would, for example, be sprayable.

In addition, low-viscosity preparations of the prior art often have the disadvantage that they are unstable and are limited to a narrow range of application or to a restricted choice of starting materials. Low-viscosity products in which, for example, strong polar oils—such as the vegetable oils frequently used in commercially available products—are sufficiently stabilized cannot therefore be currently found on the market.

O/W emulsions with a low viscosity and which have a storage stability which is required for marketable products can only be formulated according to the prior art in a very complex manner. Accordingly, the supply of such formulations is extremely low. Nevertheless, such formulations could offer the consumer cosmetic effects which are hitherto unknown.

An object of the present invention was to provide preparations which have a very low viscosity and do not have the disadvantages of the prior art.

Surprisingly, these objects are achieved by low-viscosity cosmetic or dermatological preparations comprising (I) one or more partially neutralized esters of monoglycerides and/or diglycerides of saturated fatty acids with citric acid, (II) one or more fatty alcohols chosen from the group of branched and unbranched alkyl alcohols having 12 to 40 carbon atoms, (III) a water phase, (IV) from 0 to 10% by weight of a lipid phase, based on the total weight of the preparations, where the weight ratio of the sum of the constituents from (I) and (II): (IV) is chosen from the range from 20:1 to 1:5.

It had therefore not been foreseen by the person skilled in the art that the preparations according to the invention would be more effective as moisture-donating preparations, would be easier to formulate, would better promote skin smoothing, would be characterized by a better care action, would be better vehicles for cosmetic and medicinal-dermatological active ingredients, would have better sensory properties, such as, for example, the dispersibility on the skin or absorption into the skin, have higher stability against splitting into oil and water phases, and would exhibit better biocompatibility than the preparations of the prior art.

The preparations according to the invention therefore represent an enrichment of the prior art with regard to flowable O/W emulsions.

The invention further relates to the use of (I) one or more partially neutralized esters of monoglycerides and/or diglycerides of saturated fatty acids with citric acid, (II) one or more fatty alcohols chosen from the group of branched and unbranched alkyl alcohols having 12 to 40 carbon atoms, (III) a water phase, (IV) from 0 to 10% by weight of a lipid phase, based on the total weight of the preparations, where the weight ratio of the sum of the constituents from (I) and (II): (IV) is chosen from the range of from 20:1 to 1:5, for the preparation of low-viscosity preparations, in particular of O/W emulsions.

The lipid content of the preparations obtainable according to the invention can advantageously be varied from 0% by weight up to 10% by weight, with equally favourable results being achieved. In cases where no lipid is present, the system is not an emulsion, but a system which is most appropriately referred to as an emulsifier gel.

Preparations according to the invention preferably comprise up to 7.5% by weight of a lipid phase and are then O/M emulsions. Preparations according to the invention particularly advantageously comprise up to 6% by weight of a lipid phase. Preparations according to the invention particularly preferably comprise 2 to 4% by weight of a lipid phase, in particular about 3% by weight, in each case based on the total weight of the preparations.

According to the teaching presented herein, O/M emulsions are obtainable whose viscosity at 25° C. is less than 2500 mPa·s (=millipascal seconds), in particular less than 2000 mPa·s (measured using a Viscotester VT-02, Haake).

A particularly advantageous citric ester is glyceryl stearate citrate. Such citric esters are obtainable, for example, under the product name "IMWITOR® 370" from Hüls AG.

The total amount of one or more glycerol esters of α-hydroxycarboxylic acids and saturated fatty acids used according to the invention in the finished cosmetic or dermatological preparations is advantageously chosen from the range 0.1–10.0% by weight, preferably 0.5–6.0% by weight, based on the total weight of the preparations.

The preferred fatty alcohol used according to the invention is cetylstearyl alcohol (a mixture of 1-hexadecanol and 1-octadecanol in equal amounts).

The total amount of one or more fatty alcohols used according to the invention in the finished cosmetic or dermatological preparations is advantageously chosen from the range 0.1–10.0% by weight, preferably 0.5–6.0% by weight, based on the total weight of the preparations.

According to the invention, it is advantageous to choose weight ratios of one or more partially neutralized esters of monoglycerides and/or diglycerides of saturated fatty acids with citric acid on the one hand and fatty alcohols on the other hand of from 10:1 to 1:5, preferably from 6:1 to 1:1, particularly preferably of about 3:1.

The weight ratio of the total of the constituents of one or more partially neutralized esters of monoglycerides and/or diglycerides of saturated fatty acids with citric acid, and fatty alcohols to the oil phase is chosen according to the invention from the range from 20:1 to 1:5, advantageously from the range from 20:1 to 1:2, particularly preferably about 1:1.

The oil phase of the O/W emulsions according to the invention is advantageously chosen from the group of lecithins and of fatty acid triglycerides, namely the triglycerol esters of saturated and/or unsaturated, branched and/or unbranched alkanecarboxylic acids having a chain length of from 8 to 24 carbon atoms, in particular 12 to 18 carbon atoms. The fatty acid triglycerides can, for example, be advantageously chosen from the group of synthetic, semi-synthetic and natural oils, such as, for example, olive oil, sunflower oil, soya oil, peanut oil, rapeseed oil, almond oil, palm oil, coconut oil, castor oil, wheatgerm oil, grapeseed oil, thistle oil, evening primrose oil and the like.

The oils according to the invention are likewise advantageously chosen from the group consisting of Vaseline (petrolatum), paraffin oil and polyolefins. Of the polyolefins, polydecenes are the preferred substances.

For the purposes of the present invention, the oil phase can additionally advantageously be chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, and from the group of esters of aromatic carboxylic acids and saturated and/or unsaturated, branched and/or unbranched alcohols having a chain length of from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, such as, for example, jojoba oil.

The oil phase can also advantageously be chosen from the group of branched and unbranched hydrocarbons and hydrocarbon waxes, silicone oils, dialkyl ethers, and the group of saturated or unsaturated, branched or unbranched alcohols.

Any desired mixtures of such oil and wax components can also be used advantageously for the purposes of the present invention. In some cases, it may also be advantageous to use waxes, for example cetyl palmitate, as the sole lipid component of the oil phase.

Of the hydrocarbons, paraffin oil, squalane and squalene are used advantageously for the purposes of the present invention.

The oil phase can advantageously also have a content of cyclic or linear silicone oils or consist entirely of such oils, although it is preferable to use an additional content of other oil phase components apart from the silicone oil or the silicone oils.

Cyclomethicone (octamethylcyclotetrasiloxane) is advantageously used as the silicone oil to be used according to the invention. However, other silicone oils can also be used advantageously for the purposes of the present invention, for example hexamethylcyclotrisiloxane, polydimethylsiloxane and poly(methylphenylsiloxane).

The aqueous phase of the preparations according to the invention in some instances advantageously comprises alcohols, diols or polyols of low carbon number, and ethers thereof, preferably ethanol, isopropanol, propylene glycol, glycerol, ethylene glycol, ethylene glycol monoethyl ether or monobutyl ether, propylene glycol monomethyl, monoethyl or monobutyl ethers, diethylene glycol monomethyl or monoethyl ethers and analogous products, and also alcohols of low carbon number, e.g. ethanol, isopropanol, 1,2-propanediol, glycerol and, in particular, one or more thickeners which can advantageously be chosen from the group consisting of silicon dioxide, aluminium silicates, polysaccharides or derivatives thereof, e.g. hyaluronic acid, xanthan gum, hydroxypropylmethylcellulose, particularly advantageously from the group consisting of polyacrylates, preferably a polyacrylate from the group of carbopols, for example carbopol grades 980, 981, 1382, 2984, 5984, or also ETD (easy-to-disperse) grades 2001, 2020, 2050, in each case individually or in any combinations with one another.

Particularly advantageous preparations are also obtained when antioxidants are used as additives or active ingredients. According to the invention, the preparations advantageously comprise one or more antioxidants. Antioxidants which are favourable but which are nevertheless optional may be all antioxidants which are customary or suitable for cosmetic and/or dermatological applications.

The antioxidants are advantageously selected from the group consisting of amino acids (e.g. glycine, histidine, tyrosine, tryptophan) and derivatives thereof, imidazoles, (e.g. urocanic acid) and derivatives thereof, peptides, such as D,L-camosine, D-camosine, L-camosine and derivatives thereof (e.g. anserine), carotenoids, carotenes (e.g. α-carotene, βcarotene, ψlycopene) and derivatives thereof, lipoic acid and derivatives thereof (e.g. dihydrolipoic acid), aurothioglucose, propylthiouracil and other thiols (e.g. thioredoxin, glutathione, cysteine, cystne, cystamine and the glycosyl, N-acetyl, methyl, ethyl, propyl, amyl, butyl and lauryl, paimitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (e.g. buthionine sulphoximines, homocysteine sulphoximine, buthionine sulphones, penta-, hexa-, heptathionine sulphoximine) in very low tolerated doses (e.g. pmol to $\mu$mol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active substances which are suitable according to the invention.

For the purposes of the present invention, oil-soluble antioxidants can be used particularly advantageously.

A surprising property of the present invention is that preparations according to the invention are very good vehicles for cosmetic or dermatological active ingredients into the skin, preferred active ingredients being antioxidants which are able to protect the skin against oxidative stress. Preferred antioxidants are vitamin E and derivatives thereof and vitamin A and derivatives thereof.

The amount of antioxidants (one or more compounds) in the preparations is preferably from 0.001 to 30% by weight, particularly preferably 0.05–20% by weight, in particular 1–10% by weight, based on the total weight of the preparation.

If vitamin E and/or its derivatives are used as the antioxidant or antioxidants, the respective concentrations thereof are advantageously chosen from the range 0.001–10% by weight, based on the total weight of the formulation.

If vitamin A or vitamin A derivatives or carotenes or derivatives thereof are used as the antioxidant or antioxidants, the respective concentrations thereof are advantageously chosen from the range 0.001–10% by weight, based on the total weight of the formulation.

The person skilled in the art is of course aware that cosmetic preparations are in most cases inconceivable without the customary auxiliaries and additives. The cosmetic and dermatological preparations according to the invention can, accordingly, also comprise cosmetic auxiliaries, as are customarily used in such preparations, for example bodying agents, stabilizers, fillers, preservatives, perfumes, antifoams, dyes, pigments which have a colouring action, thickeners, surface-active substances, emulsifiers, emollients, moisturizers and/or humectants, antiinflammatory substances, additional active ingredients such as vitamins or proteins, sunscreens, insect repellants, bactericides, virucides, water, salts, antimicrobial, proteolytic or keratolytic substances, medicaments or other customary constituents of a cosmetic or dermatological formulation such as alcohols, polyols, polymers, foam stabilizers, organic solvents or also electrolytes.

The latter can be chosen, for example, from the group of salts containing the following anions: chlorides, also inorganic oxo element anions, of these, in particular sulphates, carbonates, phosphates, borates and aluminates. Electrolytes based on organic anions are also advantageous, e.g. lactates, acetates, benzoates, propionates, tartrates, citrates, amino acids, ethylenediaminetetraacetic acid and salts thereof and others. Preferred cations of the salts are ammonium, alkylammonium, alkali metal, alkaline earth metal, magnesium, iron or zinc ions. It does not need to be mentioned that only physiologically acceptable electrolytes should be used in cosmetics. Particular preference is given to potassium chloride, sodium chloride, magnesium sulphate, zinc sulphate and mixtures thereof.

Corresponding requirements apply mutatis mutandis to the formulation of medicinal preparations.

The O/W emulsions according to the invention can be used as a basis for cosmetic or dermatological formulations. The latter can have the customary composition and be used, for example, for the treatment and care of the skin and/or the hair, as lip care product, as deodorant product and as make-up or make-up remover product in decorative cosmetics or as a sunscreen preparation. For use, the cosmetic and dermatological preparations according to the invention are applied to the skin and/or the hair in a sufficient amount in a manner customary for cosmetics or dermatological compositions.

For the purposes of the present invention, cosmetic or topical dermatological compositions can accordingly, depending on their composition, be used, for example, as a skin protection cream, cleansing milk, sunscreen lotion, nourishing cream, day or night cream, etc. In some circumstances it is possible and advantageous to use the compositions according to the invention as a base for pharmaceutical formulations.

The low-viscosity cosmetic or dermatological compositions according to the invention can, for example, be in the form of preparations which can be sprayed from aerosol containers, squeezable bottles or by means of a pump device, or in the form of a liquid composition which can be applied by means of roll-on devices, but also in the form of an emulsion which can be applied from normal bottles and containers.

Suitable propellants for cosmetic or dermatological preparations which can be sprayed from aerosol containers for the purposes of the present invention are the customary known readily volatile, liquefied propellants, for example hydrocarbons (propane, butane, isobutane), which can be used alone or in a mixture with one another. Compressed air is also used advantageously.

The person skilled in the art is of course aware that there are propellants which are non-toxic per se which would be suitable in principle for realizing the present invention in the form of aerosol preparations, but which must nevertheless be avoided because of their unacceptable impact on the environment or other accompanying circumstances, in particular fluorinated hydrocarbons and chlorofluorocarbons (CFCs).

Cosmetic and dermatological preparations which are in the form of a sunscreen are also favourable. As well as the active ingredient combinations according to the invention, these preferably additionally comprise at least one UV-A filter substance and/or at least one UV-B filter substance and/or at least one inorganic pigment.

For the purposes of the present invention, however, it is also advantageous to provide cosmetic and dermatological preparations whose main purpose is not protection against sunlight, but which nevertheless have a content of UV protectants. Thus, for example, UV-A or UV-B filter substances are usually incorporated into day creams.

UV protectants, like antioxidants and, if desired, preservatives, also effectively protect the preparations themselves against decay.

Preparations according to the invention can furthermore advantageously comprise substances which absorb UV radiation in the UV-B range, the total amount of filter substances being, for example, from 0.1% by weight to 30% by weight, preferably from 0.5 to 10% by weight, in particular from 1.0 to 6.0% by weight, based on the total weight of the preparations, in order to provide cosmetic preparations which protect the hair and/or the skin from the entire region of ultraviolet radiation. They can also be used as sunscreens for the hair or the skin.

If the emulsions according to the invention contain UV-B filter substances, the latter may be oil-soluble or water-soluble. Examples of oil-soluble UV-B filters which are advantageous according to the invention are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino) benzoate;

esters of cinnamic acid, preferably 2-ethylhexyl 4-methoxycinnamate, isopentyl 4-methoxycinnamate;

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzo-phenone;

esters of benzalmalonic acid, preferably di(2-ethylhexyl) 4-methoxybenzalmalonate;

derivatives of 1,3,5-triazine, preferably 2,4,6-trianilino(p-carbo-2'-ethyl-1'-hexyloxy)-1,3,5-triazine.

The list of said UV-B filters, which may be used in combination with the active ingredient combinations according to the invention is of course not intended to be limiting.

It can also be advantageous to formulate lipodispersions according to the invention with UV-A filters which have hitherto been customarily present in cosmetic preparations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)-propane-1,3-dione.

Cosmetic and dermatological preparations according to the invention can also comprise inorganic pigments which are customarily used in cosmetics for protecting the skin against UV rays. These are oxides of titanium, zinc, iron, zirconium, silicon, manganese, aluminium, cerium and mixtures thereof, and modifications in which the oxides are the active agents. Particular preference is given to pigments based on titanium dioxide.

Further constituents which can be used are:

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids;

alcohols, diols or polyols of low carbon number, and ethers thereof, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products.

The examples below serve to illustrate the present invention without limiting it. The numerical values in the examples refer to percentages by weight, based on the total weight of the respective preparations.

EXAMPLE 1 (O/W EMULSION)

|  | % by weight |
|---|---|
| Glyceryl stearate citrate | 3.00 |
| Stearyl alcohol | 1.00 |
| Octyldodecanol | 1.00 |
| Caprylic/capric triglyceride | 1.00 |
| Dicaprylyl ether | 1.00 |
| Carbomer | 0.15 |
| Glycerol | 3.00 |
| Perfume, preservatives, NaOH dyes, antioxidants etc. | q.s. |
| Water | ad 100,00 |
| pH adjusted to | 5.5 |

EXAMPLE 2 (O/W EMULSION)

|  | % by weight |
|---|---|
| Glyceryl stearate citrate | 3.00 |
| Stearyl alcohol | 1.00 |
| Octyldodecanol | 0.25 |
| Caprylic/capric triglyceride | 0.25 |
| Dicaprylyl ether | 0.25 |
| Carbomer | 0.15 |
| Glycerol | 3.00 |
| Perfume, preservatives, NaOH dyes, antioxidants etc. | q.s. |
| Water | ad 100,00 |
| pH adjusted to | 5.5 |

EXAMPLE 3 (O/W EMULSION)

|  | % by weight |
|---|---|
| Glyceryl stearate citrate | 3.00 |
| Behenyl alcohol | 1.00 |
| Dimethicone | 1.50 |
| Cyclomethicone | 1.50 |
| Carbomer | 0.15 |
| Glycerol | 6.00 |
| Perfume, preservatives, NaOH dyes, antioxidants etc. | q.s. |
| Water | ad 100.00 |
| pH adjusted to | 5.5 |

EXAMPLE 4 (O/W EMULSION)

|  | % by weight |
|---|---|
| Glyceryl stearate citrate | 3.00 |
| Stearyl alcohol | 1.00 |
| Octyldodecanol | 0.25 |
| Caprylic/capric triglyceride | 0.25 |
| Dicaprylyl ether | 0.25 |
| Dimethicone | 0.50 |
| Carbomer | 0.15 |
| Glycerol | 3.00 |
| Aluminium starch octenyl succinate | 0.50 |
| Talc | 0.50 |
| Bentonites | 0.50 |
| Perfume, preservatives, NaOH dyes, antioxidants etc. | q.s. |
| Water | ad 100.00 |
| pH adjusted to | 5.5 |

EXAMPLE 5 (O/W EMULSION)

|  | % by weight |
|---|---|
| Glyceryl stearate citrate | 3.00 |
| Cetyl alcohol | 1.00 |
| Squalane | 1.00 |
| Jojoba oil | 1.00 |
| Paraffinum liquidum | 1.00 |
| Carbomer | 0.10 |
| Glycerol | 3.00 |
| Serine | 0.50 |
| Tocopherol acetate | 1.00 |
| Carbomer | 0.10 |
| Xanthan gum | 0.10 |
| Perfume, preservatives, NaOH dyes, antioxidants etc. | q.s. |
| Water | ad 100.00 |
| pH adjusted to | 6.0 |

EXAMPLE 6 (O/W EMULSION)

|  | % by weight |
|---|---|
| Glyceryl stearate citrate | 3.00 |
| Cetyl alcohol | 0.50 |
| Octyldodecanol | 0.40 |
| Caprylic/capric triglyceride | 0.40 |
| Dicaprylyl ether | 0.40 |
| Carbomer | 0.10 |
| Glycerol | 3.00 |
| Serine | 0.50 |
| Perfume, preservatives, NaOH dyes, antioxidants etc. | q.s. |
| Water | ad 100.00 |
| pH adjusted to | 5.5 |

EXAMPLE 7 (EMULSIONS MAKE-UP)

|  | % by weight |
|---|---|
| Glyceryl stearate citrate | 3.00 |
| Stearyl alcohol | 1.00 |
| Dimethicone | 0.50 |
| Glycerol | 1.50 |
| 1,3-Butylene glycol | 1.50 |
| Magnesium silicate | 1.00 |
| Mica | 1.00 |
| Iron oxides | 1.00 |
| Titanium dioxide | 2.50 |
| Talc | 5.00 |
| Carbomer | 0.15 |
| Perfume, preservatives, NaOH, dyes, antioxidants etc. | q.s. |
| Water | ad 100.00 |
| pH adjusted to | 5.5 |

EXAMPLE 8 (O/W EMULSION)

|  | % by weight |
|---|---|
| Glyceryl stearate citrate | 3.00 |
| Stearyl alcohol | 1.00 |
| Octyldodecanol | 0.25 |
| Caprylic/capric triglyceride | 0.25 |
| Dicaprylyl ether | 0.25 |
| Octyl methoxycinnamate | 4.00 |
| Benzophenone-3 | 3.00 |
| Octyl salicylate | 3.00 |
| Carbomer | 0.15 |
| Glycerol | 3.00 |
| Perfume, preservatives, NaOH dyes, antioxidants etc. | q.s. |
| Water | ad 100.00 |
| pH adjusted to | 5.5 |

EXAMPLE 9 (O/W EMULSION)

|  | % by weight |
|---|---|
| Glyceryl stearate citrate | 3.00 |
| Stearyl alcohol | 1.00 |
| Octyldodecanol | 0.50 |
| Caprylic/capric triglyceride | 0.50 |
| Dicaprylyl ether | 0.50 |
| Distarch phosphate | 1.00 |
| Ethanol | 10.00 |
| Carbomer | 0.15 |
| Glycerol | 3.00 |
| Perfume, preservatives, NaOH dyes, antioxidants etc. | q.s. |
| Water | ad 100.00 |
| pH adjusted to | 5.5 |

EXAMPLE 10 (EMULSIFIER GEL)

|  | % by weight |
|---|---|
| Glyceryl stearate citrate | 3.00 |
| Stearyl alcohol | 1.00 |
| Ethanol | 2.00 |
| Aluminium starch octenyl succinate | 0.25 |
| Talc | 0.25 |
| Tapioca starch | 0.25 |
| Carbomer | 0.15 |
| Glycerol | 3.00 |
| Perfume, preservatives, NaOH dyes, antioxidants etc. | q.s. |

| | % by weight |
|---|---|
| Water | ad 100.00 |
| pH adjusted to | 5.5 |

What is claimed is:

1. Cosmetic or dermatological O/W emulsion preparations with a viscosity of less than 2500 mPa·s at 25° C. comprising
   (I) from 0.1 to 10% by weight of one or more partially neutralized esters of monoglycerides and/or diglycerides of saturated fatty acids with citric acid,
   (II) one or more fatty alcohols chosen from the group of branched and unbranched alkyl alcohols having 12 to 40 carbon atoms,
   (III) a water phase,
   (IV) from 2 to 10% by weight of a lipid phase, based on the total weight of the preparations,
where the weight ratio of the sum of the constituents from (I) and (II): (IV) is chosen from the range from 20:1 to 1:5.

2. Preparations according to claim 1, characterized in that the partially neutralized ester of monoglycerides and/or diglycerides of saturated fatty acids with citric acid chosen is glyceryl stearate citrate.

3. Preparations according to claim 1, characterized in that the fatty alcohol chosen is cetylstearyl alcohol.

4. Preparations according to claim 1, characterized in that the total amount of one or more fatty alcohols used according to the invention in the finished cosmetic or dermatological preparations is chosen from the range 0.1–10.0% by weight based on the total weight of the preparations.

5. Preparations according to claim 1, characterized in that weight ratios of one or more partially neutralized esters of monoglycerides and/or diglycerides of saturated fatty acids with citric acid on the one hand and fatty alcohols on the other hand are chosen from the range 10:1 to 1:10.

6. The preparations of claim 1 characterized in that the total amount of one or more partially neutralized esters of monoglycerides and/or diglycerides or saturated fatty acids with citric acid in the finished cosmetic or dermatological preparations is chosen from the range 0.5–6.0% by weight, based on the total weight of the preparations.

7. Preparations according to claim 4, characterized in that the total amount of one or more fatty alcohols used according to the invention in the finished cosmetic or dermatological preparations is chosen from the range 0.5–6.0% by weight based on the total weight of the preparations.

8. Preparations according to claim 5, characterized in that weight ratios of one or more partially neutralized esters of monoglycerides and/or diglycerides of saturated fatty acids with citric acid on the one hand and fatty alcohols on the other hand are chosen from the range 2:1 to 1:2.

9. Preparations according to claim 8, characterized in that weight ratios of one or more partially neutralized esters of monoglycerides and/or diglycerides of saturated fatty acids with citric acid on the one hand and fatty alcohols on the other hand is 1:1.

10. Preparations according to claim 1, characterized in that the weight ratio of the sum of constituents of partially neutralized esters of monoglycerides and/or diglycerides of saturated fatty acids with citric acid and fatty alcohols to the lipid phase is chosen from the range 20:1 to 1:2.

11. Preparations according to claim 10, characterized in that the weight ratio of the sum of constituents of partially neutralized esters of monoglycerides and/or diglycerides of saturated fatty acids with citric acid and fatty alcohols to the lipid phase is 1:1.

* * * * *